United States Patent
Jakobsson et al.

(10) Patent No.: US 10,675,585 B2
(45) Date of Patent: Jun. 9, 2020

(54) METHOD FOR THE REMOVAL OF OXYGEN FROM AN INDUSTRIAL GAS

(71) Applicant: HALDOR TOPSØE A/S, Kgs. Lyngby (DK)

(72) Inventors: Niklas Bengt Jakobsson, Kågeröd (SE); Kresten Egeblad, Farum (DK); Jacob Hjerrild Zeuthen, Birkerød (DK); Rasmus Trane-Restrup, Roskilde (DK)

(73) Assignee: Haldor Topsoe A/S, Lyngby (DK)

( * ) Notice: Subject to any disclaimer, the term of this patent is extended or adjusted under 35 U.S.C. 154(b) by 0 days.

(21) Appl. No.: 16/093,998

(22) PCT Filed: May 3, 2017

(86) PCT No.: PCT/EP2017/060511
§ 371 (c)(1),
(2) Date: Oct. 16, 2018

(87) PCT Pub. No.: WO2017/202582
PCT Pub. Date: Nov. 30, 2017

(65) Prior Publication Data
US 2019/0126201 A1 May 2, 2019

(30) Foreign Application Priority Data

May 24, 2016 (DK) .......................... PA 2016 00309
Oct. 17, 2016 (DK) .......................... PA 2016 00634

(51) Int. Cl.
*B01D 53/86* (2006.01)
*B01D 53/75* (2006.01)
(Continued)

(52) U.S. Cl.
CPC .......... *B01D 53/869* (2013.01); *B01D 53/02* (2013.01); *B01D 53/507* (2013.01); *B01D 53/75* (2013.01);
(Continued)

(58) Field of Classification Search
None
See application file for complete search history.

(56) References Cited

U.S. PATENT DOCUMENTS 4,406,777 A * 9/1983 Melconian ............. C10G 51/02
208/152
8,211,211 B1 * 7/2012 Knaebel ................. B01D 53/75
95/119
(Continued)

FOREIGN PATENT DOCUMENTS

CN 102433184 A 5/2012
CN 102839028 A 12/2012
(Continued)

OTHER PUBLICATIONS

CN-103159580-A English Translation (Year: 2014).*

*Primary Examiner* — Anita Nassiri-Motlagh
(74) *Attorney, Agent, or Firm* — Blank Rome LLP

(57) ABSTRACT

Oxygen is removed from a gas feed such as a landfill gas, a digester gas or an industrial $CO_2$ off-gas by removing sulfur-containing compounds and siloxanes from the feed gas, heating the feed gas, injecting one or more reactants for oxygen conversion into the heated feed gas, carrying out a selective catalytic oxygen conversion in at least one suitable reactor and cleaning the resulting oxygen-depleted gas. The reactants to be injected comprise one or more of $H_2$, CO, ammonia, urea, methanol, ethanol and dimethylether (DME).

14 Claims, 1 Drawing Sheet

Figure 1:
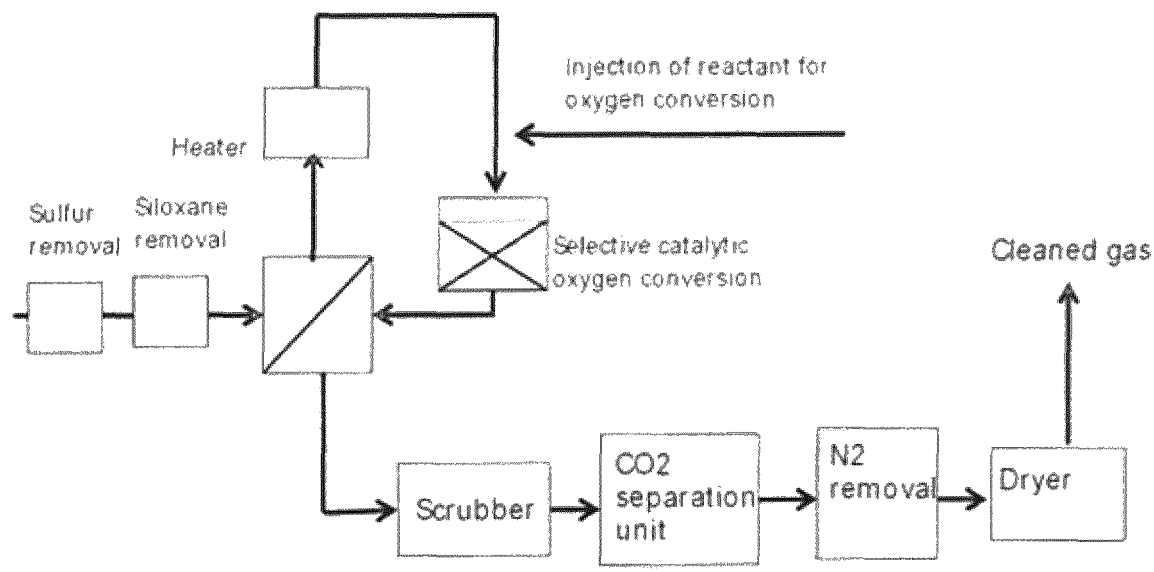

(51) Int. Cl.
  *C12M 1/00* (2006.01)
  *C10L 3/10* (2006.01)
  *B01D 53/02* (2006.01)
  *B01D 53/50* (2006.01)
  *B01D 53/78* (2006.01)
  *B01D 53/72* (2006.01)

(52) U.S. Cl.
  CPC ......... *B01D 53/78* (2013.01); *B01D 53/8603* (2013.01); *B01D 53/8671* (2013.01); *C10L 3/101* (2013.01); *C10L 3/103* (2013.01); *C10L 3/104* (2013.01); *C12M 47/18* (2013.01); *B01D 53/50* (2013.01); *B01D 53/72* (2013.01); *B01D 2251/20* (2013.01); *B01D 2251/604* (2013.01); *B01D 2257/102* (2013.01); *B01D 2257/104* (2013.01); *B01D 2257/504* (2013.01); *B01D 2257/556* (2013.01); *B01D 2257/80* (2013.01); *B01D 2258/05* (2013.01); *C10L 2230/02* (2013.01); *C10L 2290/08* (2013.01); *C10L 2290/26* (2013.01); *C10L 2290/545* (2013.01); *Y02E 50/346* (2013.01)

(56) References Cited

U.S. PATENT DOCUMENTS

| | | |
|---|---|---|
| 2012/0128561 A1 | 5/2012 | Blair et al. |
| 2013/0095014 A1 | 4/2013 | Grill |
| 2013/0108531 A1 | 5/2013 | Mitariten |
| 2013/0209338 A1 | 8/2013 | Prasad et al. |
| 2015/0119623 A1 | 4/2015 | Huang |
| 2015/0203772 A1* | 7/2015 | Schoch .................. C10L 3/101 585/824 |

FOREIGN PATENT DOCUMENTS

| | | | |
|---|---|---|---|
| CN | 102952590 A | | 3/2013 |
| CN | 103159580 A | * | 6/2013 |
| EP | 1 997 549 B1 | | 9/2010 |
| GB | 2466554 A | | 6/2010 |
| JP | 2012-214808 A | | 11/2012 |
| KR | 2015-0082103 A | | 7/2015 |
| WO | WO 2004/056449 A2 | | 7/2004 |
| WO | WO 2010/073026 A1 | | 7/2010 |
| WO | WO 2011/097162 A1 | | 8/2011 |
| WO | WO 2012/006729 A1 | | 1/2012 |
| WO | WO 2015/057752 A1 | | 4/2015 |

* cited by examiner

METHOD FOR THE REMOVAL OF OXYGEN FROM AN INDUSTRIAL GAS

The present invention relates to a novel method for the removal of oxygen from an industrial gas through selective catalytic oxidation via reactant injection.

More specifically, the invention concerns an alternative route to reduce the oxygen content in industrial gases, where the reduction of the content of oxygen is crucial for the valorization of the gas. The method of the invention is focusing on landfill gas, digester gas and industrial $CO_2$ off-gas. Today, oxygen removal is accomplished through PSA (pressure swing adsorption), membrane or scrubber technologies with very high capital expenditure (CAPEX) and also a substantial loss of valuable components, such as methane in the main gas to the oxygen-containing off-gas. The present invention comprises addition of components, such as $H_2$, CO, methanol, ammonia or ethanol, to the main gas stream and leading the resultant gas stream to at least one catalytic reactor. In said reactor(s), the oxygen is converted selectively to $CO_2$ and water across the catalyst.

Removal of oxygen from fuel gas streams is often a requirement for distribution of the gas in the natural gas grid, and it is also a requirement when utilizing the gas as a vehicle transportation fuel. In addition, removal of oxygen is also critical for the utilization of other industrial gas streams, such as in producing merchant or industrial grade $CO_2$ from oxygen-containing off-gases.

U.S. Pat. No. 3,361,531 describes the removal of oxygen from oxygen-containing environments and gas mixtures by absorption in a solid material contact mass. More specifically, a compound selected from copper carbonate, manganese carbonate and iron carbonate is contacted with a hydrogen-containing gas at an elevated temperature below about 500° C., thereby reducing the carbonate to the corresponding oxide compound. This oxide compound is brought into contact with said oxygen-containing environment at around ambient temperature, thereby absorbing the oxygen and oxidizing the oxide compound.

The technologies dominating the industry today are PSA and membrane based technologies in small and medium sized projects (typically up to 10,000 Nm³/h gas), whereas distillation and cryogenic separation are the dominating technologies in larger scale applications.

For applications in the digester gas and landfill gas purification industry the gas flows are in the range of 500 to 10,000 Nm³/h, and technologies based on PSA and membranes are dominating. Apart from an often prohibitive CAPEX, PSA and membrane technologies have a high operation cost because of their complexity and gas compression as well as a substantial loss of valuable hydrocarbons, such as methane, from the feed gas stream to the oxygen containing waste gas stream.

In the method according to the present invention, one or more components suitable for catalytic oxidation are injected into the oxygen-containing main gas stream after removal of sulfur-containing compounds and siloxanes from the gas. The components and the catalyst are chosen so that the catalyst oxidizes the injected components using the oxygen in the stream without substantially oxidizing the valuable components, such as methane, in the gas stream.

The components to be injected may comprise one or more of i.a. $H_2$, CO, ammonia, urea, ethanol and dimethylether (DME).

The active catalyst may comprise a metal selected among vanadium, tungsten, chromium, copper, manganese, molybdenum, platinum, palladium, rhodium and ruthenium in metallic or metal oxide form supported on a carrier selected from alumina, titania, silica and ceria and combinations thereof.

Sulfur impurities in an industrial gas can create a corrosive environment inside power generating equipment or even poison catalysts that may be present. In addition, hydrogen sulfide present in the feed gas to gas engines will cause degradation of the lubricating oil and lead to a need of frequent maintenance. Furthermore, $H_2S$ needs to be removed if the gas is to be sent to gas pipelines or used as fuel in vehicles.

Another reason to clean the gas is that other impurities, such as siloxanes, can be deposited within heat and power generation equipment and cause significant damage to the internal components.

Siloxanes are organosilicon compounds comprising silicon, carbon, hydrogen and oxygen which have Si—O—Si bonds. Siloxanes can be linear as well as cyclic. They may be present in biogas because they are used in various beauty products, such as e.g. cosmetics and shampoos that are washed down drains or otherwise disposed of, so that they end up in municipal wastewater and landfills. Siloxanes are not broken down during anaerobic digestion, and as a result, waste gas captured from treatment plants and landfills is often heavily contaminated with these compounds. It is known that siloxanes can be removed using non-regenerative packed bed adsorption with activated carbon or porous silica as sorbent. Regenerative sorbents can also be used as well as units based on gas cooling to very low temperatures to precipitate the siloxanes out from the gas. Further, liquid extraction technologies are used. In addition, these technologies can be used in combination.

So a major issue in the utilization of raw gas from landfills and anaerobic digesters is to provide a gas stream with a low sulfur content, i.e. less than a few hundred ppm, and with a very low content of siloxanes, typically linear or cyclic dimethyl Si—O—Si compounds. The pipeline specifications for natural gas are even stricter. In this case, $H_2S$ must be removed to a residual concentration below 5 ppm, and $CO_2$ and $N_2$ need to be removed as well. Combustion of sulfur containing compounds leads to formation of sulfur trioxide which will react with moisture in the gas to form sulfuric acid, which can condense in cold spots and lead to corrosion. However, particularly siloxanes give rise to problems because they are converted to $SiO_2$ during combustion, leading to build-up of abrasive solid deposits inside the engine and causing damage, reduced service time and increased maintenance requirements for many components such as compressors, fans, blowers, burner nozzles, heat recovery surfaces in boilers and for gas engine components such as spark plugs, valves, pistons etc. In addition to causing damage and reduced service time to the engine, also any catalysts installed to control exhaust gas emissions are sensitive to $SiO_2$ entrained in the gas stream, in fact even more so than the engine itself. For an SCR (selective catalytic reduction) catalyst, for example, the $SiO_2$ tolerance can be as low as 250 ppb.

For the reasons outlined above it is very desirable to remove siloxanes and sulfur-containing compounds from gas streams.

Thus, the present invention relates to a method for the removal of oxygen from an industrial gas feed, said process comprising the steps of:

(a) removing sulfur-containing compounds and siloxanes from the feed gas, (b) injecting one or more reactants for oxygen conversion into the heated feed gas, (c) carrying out a selective catalytic oxygen conversion in at least one suitable reactor, and (d) cleaning the resulting oxygen-depleted gas, wherein the feed gas is heated either prior to or following step (a).

Conventionally the siloxanes and sulfur-containing compounds have been removed from gas streams at low temperatures, i.e. before heating the gas stream. However, it is also possible to fit the oxygen conversion more closely to a design in which the removal of the sulfur-containing compounds and siloxanes from the feed gas is part of the hot loop, i.e. with heating of the gas stream prior to removing the siloxanes and sulfur-containing compounds from it.

Preferably the gas feed, from which oxygen is to be removed, is a landfill gas, a digester gas or an industrial $CO_2$ off-gas.

In a preferred embodiment of the method of the invention, a gas stream, such as a landfill gas containing $H_2S$ and organic sulfur along with siloxanes, $CO_2$, $H_2O$, methane and various VOC (volatile organic carbon) compounds is treated.

The components to be injected in step (c) comprise one or more of $H_2$, CO, ammonia, urea, methanol, ethanol and dimethylether (DME).

Landfill gas of low quality, i.e. having a high content of nitrogen and oxygen, is more difficult and expensive to upgrade to pipeline quality than gases with a lower content of nitrogen and oxygen. Using the reactant injection to remove the oxygen from low quality landfill gases will lead to a high temperature increase in the reactor, which in turn will damage the catalyst. If, however, the reactant is dosed at two different points instead of one point, it is possible to use two reactors in series with cooling and reactant injection in between. This approach has the added benefit that the energy recovered after each reactor can be used in a reboiler in the $CO_2$ separation unit (amine wash) to regenerate the amine, and it can also be used as a feed preheater. The energy for the reboiler and for preheating of the feed would otherwise have to come from electricity or from combustion of landfill gas or natural gas.

The heat coming from the oxidation can be transferred to an oil circuit which is used both to run a reboiler in the amine wash in the subsequent $CO_2$ removal and to preheat the feed.

Figure 2:
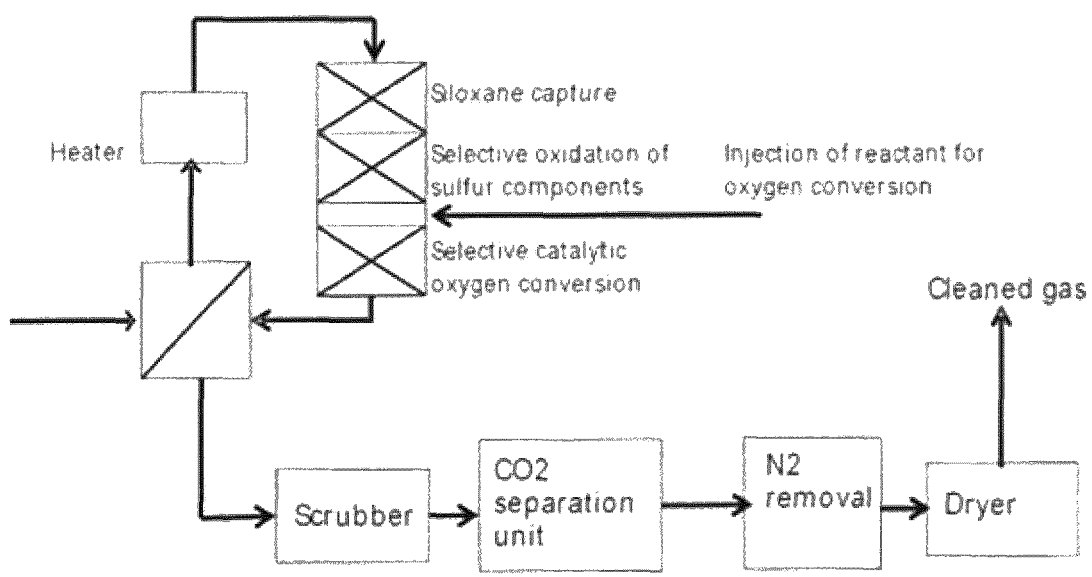

The invention is illustrated further with reference to the Figures, where FIG. 1 shows the general outline of the method, while FIG. 2 illustrates a more attractive configuration.

In the general case shown in FIG. 1, the process described above is applied after sulfur and siloxane removal using regenerative or non-regenerative adsorption technology along with gas cooling and refrigeration. After sulfur and siloxane removal, the gas is heated to between 150 and 450° C., and then $H_2$, CO, ammonia, urea, methanol, ethanol, DME or any combination thereof is injected into the main stream. Then the stream is led to the selective catalytic oxygen removal reactor, in which oxygen reacts with the injected component(s) to form $CO_2$ and water. The hot reactor exit gas can be utilized to heat the reactor inlet gas by using a feed-effluent heat exchanger.

In addition, the hot exit gas from the catalytic reactor can be used to heat the feed gas to the sulfur and siloxane removal steps, so that these steps may operate at an elevated temperature.

Downstream from the catalytic reactor, $CO_2$ is removed using amine-based $CO_2$ removal technology, $CO_2$ water scrubbing technology or solvent-based $CO_2$ removal technology. Alternatively, $CO_2$ can be removed using PSA or membrane technology.

In an alternative configuration the nitrogen removal unit is positioned downstream from the water removal unit.

Nitrogen can be removed through PSA or membrane-based technology, and water is removed through cooling and condensation followed by a molecular sieve unit, alternatively operating in a TSA (thermal swing adsorption) configuration.

In the more attractive configuration shown in FIG. 2, for siloxane and sulfur removal the present invention is combined with Applicant's GECCO™ technology for digester and landfill gas conditioning. The feed gas is heated to 200-450° C. and fed to a siloxane absorption bed comprising alumina, alumina with nickel, silica or combinations thereof.

After siloxane removal, the gas is fed to a catalytic reactor containing a catalyst selected from tungsten, vanadium, molybdenum, platinum and palladium in metallic or metal oxide form supported on a $TiO_2$ carrier. In this catalytic reactor, the catalyst converts the sulfur compounds to $SO_2$ and the VOC compounds (not methane and light [i.e. C3 and lower] hydrocarbons) to $CO_2$ and water and also hydrogen halides if some of the VOCs are halogenated.

One or more components suitable for catalytic oxidation, i.e. $H_2$, CO, ammonia, urea, methanol, ethanol, DME etc., is/are injected into the main gas stream containing oxygen, and the gas stream is fed to the catalytic reactor containing a catalyst such as vanadium, tungsten, chromium, copper, manganese, molybdenum, platinum, palladium, rhodium or ruthenium in metallic or metal oxide form supported on a carrier selected from alumina, titania, silica and ceria or combinations thereof. In the reactor, the injected component(s) is/are selectively oxidized to $H_2O$ and $CO_2$, while the valuable hydrocarbons, such as methane and light [i.e. C3 and lower] hydrocarbons, are substantially not converted. It is preferred that the catalyst comprises tungsten, vanadium, molybdenum, platinum or palladium in metallic or metal oxide form supported on a $TiO_2$ carrier.

The hot reactor exit gas can be utilized to heat the reactor inlet gas by using a feed-effluent heat exchanger.

The additional heat generated in the oxygen removal step will provide a higher temperature difference for the feed-effluent heat exchanger, which reduces the CAPEX.

Downstream from the heat exchanger, the $SO_2$ is removed in a wet caustic or $H_2O_2$ scrubber or a dry scrubber using a caustic sorbent. After the $SO_2$ removal, $CO_2$ is removed by using amine-based technology, solvent-based $CO_2$ removal technology, water-based $CO_2$ removal technology or alternatively PSA and/or membrane technology.

Nitrogen removal can be accomplished using membrane or PSA based technology. Then water is removed by using cooling and condensation followed by a molecular sieve, alternatively in a TSA configuration. Alternatively, the nitrogen removal unit is positioned downstream from the water removal unit.

It is further preferred that the catalyst is monolithic.

The invention claimed is:

1. A method for the removal of oxygen from an industrial gas feed, said process comprising the steps of:
   (a) removing sulfur-containing compounds and siloxanes from the feed gas,
   (b) injecting one or more reactants for oxygen conversion into the feed gas,
   (c) carrying out a selective catalytic oxygen conversion in at least one suitable reactor after removing sulfur-containing compounds and siloxanes from the feed gas, wherein at least two reactors with cooling in between are used for the selective catalytic oxygen conversion, (d) cleaning the resulting oxygen-depleted gas, and (e) injecting additional one or more reactants between the at least two reactors, wherein the feed gas is heated either prior to or following step (a) and wherein the selective catalytic oxygen conversion comprises converting oxygen to $CO_2$ and water, and wherein injecting one or more reactants in step (b) and step (e) includes injecting more than one of $H_2$, CO, ammonia, urea, methanol, ethanol and dimethylether (DME).

2. A method for the removal of oxygen from an industrial gas feed, said process comprising the steps of:

(a) removing sulfur-containing compounds and siloxanes from the feed gas, (b) injecting one or more reactants for oxygen conversion into the feed gas, (c) carrying out a selective catalytic oxygen conversion in at least one suitable reactor after removing sulfur-containing compounds and siloxanes from the feed gas, and (d) cleaning the resulting oxygen-depleted gas, wherein the feed gas is heated either prior to or following step (a) and wherein the selective catalytic oxygen conversion comprises converting oxygen to $CO_2$ and water, and wherein injecting one or more reactants includes injecting more than one of $H_2$, CO, ammonia, urea, methanol, ethanol and dimethyl-ether (DME).

3. Method according to claim 2, wherein the gas feed, from which oxygen is to be removed, is a landfill gas, a digester gas or an industrial $CO_2$ off-gas.

4. Method according to claim 2, wherein the cleaning in step (d) comprises removal of $CO_2$ in a separation unit, removal of $N_2$ and drying of the cleaned gas.

5. Method according to claim 1, wherein the energy recovered after each reactor is used in a re-boiler in a $CO_2$ separation unit.

6. Method according to claim 2, wherein the feed gas is heated to a temperature of between 150° C. and 450° C. after removing the sulfur-containing compounds and siloxanes.

7. Method according to claim 2, wherein the feed gas is heated to a temperature of between 150 and 450° C. prior to removing the sulfur-containing compounds and siloxanes.

8. Method according to claim 7, wherein the feed gas to the sulfur and siloxane removal units is heated through heat exchange with an effluent gas from the selective catalytic oxygen conversion step.

9. Method according to claim 3, wherein the landfill gas contains $H_2S$ and organic sulfur along with siloxanes, $CO_2$, $H_2O$, methane and various VOC (volatile organic carbon) compounds.

10. Method according to claim 2, wherein the catalyst for the oxygen conversion comprises a metal selected among vanadium, tungsten, chromium, copper, manganese, molybdenum, platinum, palladium rhodium and ruthenium in metallic or metal oxide form supported on a carrier selected from alumina, titania, silica and ceria.

11. Method according to claim 2, wherein the step of removing sulfur-containing compounds and siloxanes comprises converting the sulfur-containing compounds to $SO_2$ through selective catalytic conversion and that the $SO_2$ is removed in a scrubber.

12. Method according to claim 11, wherein the $SO_2$ is removed in a wet caustic or $H_2O_2$ scrubber or in a dry scrubber using a caustic sorbent.

13. Method according to claim 2, wherein the selective catalytic oxygen conversion step comprises selectively converting oxygen to $H_2O$ and $CO_2$.

14. Method according to claim 2, wherein the one or more reactants and a catalyst in the selective catalytic oxygen conversion are chosen so that the catalyst oxidizes the one or more reactants without oxidizing methane in the feed stream.

* * * * *